US007521059B2

(12) United States Patent
Fenwick

(10) Patent No.: US 7,521,059 B2
(45) Date of Patent: Apr. 21, 2009

(54) KENNEL COUGH VACCINE

(76) Inventor: Bradley W. Fenwick, 1911 Bluestem Ter., Manhattan, KS (US) 66502

( * ) Notice: Subject to any disclaimer, the term of this patent is extended or adjusted under 35 U.S.C. 154(b) by 730 days.

(21) Appl. No.: 10/867,532

(22) Filed: Jun. 14, 2004

(65) Prior Publication Data

US 2007/0275016 A1 Nov. 29, 2007

(51) Int. Cl.
*A61K 39/10* (2006.01)

(52) U.S. Cl. .............. 424/253.1; 424/234.1; 424/241.1; 424/192.1; 435/69.1; 435/69.7; 435/69.9; 435/71.1; 435/252.3; 435/252.33; 435/254.2

(58) Field of Classification Search .............. 424/234.1, 424/241.1, 253.1, 192.1; 435/69.1, 69.7, 435/69.9, 71.1, 252.3, 252.33, 254.2
See application file for complete search history.

(56) References Cited

U.S. PATENT DOCUMENTS

| | | | |
|---|---|---|---|
| 4,888,169 | A | 12/1989 | Brown et al. |
| 5,019,388 | A | 5/1991 | Brown et al. |
| 5,554,371 | A | 9/1996 | Caputa et al. |
| 5,595,744 | A | 1/1997 | Chalmers et al. |
| 5,616,328 | A | 4/1997 | Roberts et al. |
| 5,666,948 | A | 9/1997 | Matson |
| 5,688,682 | A | 11/1997 | Mulks et al. |
| 5,939,064 | A | 8/1999 | Savelkoul et al. |
| 6,022,728 | A | 2/2000 | Mulks et al. |
| 6,124,432 | A | 9/2000 | Kawai et al. |
| 6,284,256 | B1 | 9/2001 | Savelkoul et al. |

OTHER PUBLICATIONS

Murphy et al. Pediatr. Infect. Dis. J. 1989. 8: S66-S68.*
Yamanaka et al (J. Pediatrics. 1993. 122(2): 212-218).*
King, et al.; Microbiology; 2001; Role of the Polymorphic Region 1 of the *Bordetella pertussis* Protein Pertactin in Immunity; vol. 147; pp. 2885-2895.
Moral, et al.; Infection and Immunity; May 1998; Molecular Characterization of the Aeromonas Hydrophila aroA Gene and Potential Use of an Auxotrophic aroA Mutant as a Live Attenuated Vaccine : vol. 66, No. 5, pp. 1813-1821.
Keil, et al.; Veterinary Microbiology; 1999; Evaluation of Canine *Bordetella bronchiseptica* Isolates Using Randomly Amplified Polymorphia DNA Fingerprinting and Ribotyping; vol. 66; pp. 41-51.
Keil, et al.; AJVR; Aug. 1999/ Strain- and Growth Condition-Dependent Variability in Outer Membrane Protein Expression by *Bordetella bronchiseptica* Isolates From Dogs; vol. 60, No. 8; pp. 1016-1022.
Keil, et al.; International Veterinary Information Service; Jan. 2000; Canine Respiratory Bordetellosis: Keeping Up With an evolving pathogen; pp. 1-6.
Keil, et al.; American Veterinary Medical Association; 1998; Role of *Bordetella bronchiseptica* in Infectious Tracheobronchitis in Dogs; vol. 212, No. 2; pp. 200-207.
Keil, et al.; American Veterinary Medical Association; 1999; Strain- and Growth Condition-Dependent Variability in Outer Membrane Protein Expression by *Bordetella bronchiseptica* Isolates From Dogs; vol. 60, No. 8; pp. 1016-1021.
Keil, et al.; Pet Services Journal; 1997; Canine Infectious Tracheobronchitis Vaccines: the Battle to Control Canine Cough; pp. 18-21.
Keil, et al.; Vaccine; 2000; Cloning and Immunologic Characterization of Truncated *Bordetella bronchiseptica* Fillamentous Hemagglutinin Fusion Protein; vol. ; pp. 860-867.
Keil; A Dissertation; 1999; Canine Bordetellosis: Improving Vaccine Efficacy Using Genetic and Antigenic Characterization of *Bordetella bronchiseptica* Isolates From Dogs; pp. 1-135.
Leclerc, et al.; Antibody respons to a Foreign Epitope Expressed at the Surface of Recombinant Bacteria: Importance of the Route of Immunization; *Vaccine*; Jun. 1989; 7(3):242-8; Abstract.
Schodel, et al.; Expression of Hepatitis B Virus Antigens in Attenuated *Salmonellae* for Oral Immunization; *Res Microbiology*; Sep.-Oct. 1990; 141(7-8):831-7; Abstract.
O'Callaghan, et al.; Immunogenicity of Foreign Peptide Epitopes Expressed in Bacterial Envelope Proteins; *Res Microbiology*; Sep.-Oct. 1990; 141(7-8): 963-9; Abstract.
Charbit, et al.; Expression of a Poliovirus Neturalization Epitope at the Surface of Recombinant Bacteria: *First Immunization* Results; *Ann Inst Pasteur Microbiology*; Jan.-Feb. 1988; 139(1):45-58; Abstract.
Olin, et al.; How to Make Sense of Pertussis Immunogenicity Data; *Clin Infect Dis.*; Dec. 2001; 33 Suppl. 4:S288-91; Abstract.
McGuirk, et al.; Pathogen-Specific T Regulatory 1 Cells Induced in the Respiratory Tract by Bacterial Molecule That Stimulates Interleukin 10 Production by Dendritic Cells: a Novel Strategy for Evasion of Protective T Helper Type 1 Responses by *Bordetella pertussis; J. Exp Med.*; Jan. 2002; 195(2):221-31; Abstract.
Stefanelli, et al.; Role of Immune Sera in the In-Vitro Phagocytosis of *Bordetella pertussis* Strains; *Microb Pathog.*; Mar. 2002; 32(3):135-41; Abstract.
Watanabe, et al.; Evaluation of Efficacy in Terms of Antibody Levels and Cell-Mediated Immunity of Acelluar Pertussis Vaccines in a Murine Model of Respiratory Infection; *Fems Immunol Med Microbiology*; Jul. 2002; 33(3):219-25; Abstract.
Lui, et al.; Reverse Transcriptase-Mediated Tropism Switching in *Bordetella* Bacteriophage; *Science*; Mar. 2002; 295(5562):2091-4; Abstract.

(Continued)

*Primary Examiner*—Jennifer E Graser
(74) *Attorney, Agent, or Firm*—Hovey Williams LLP

(57) ABSTRACT

Improved, low cost vaccines for administration to living subjects such as mammals and birds are provided, which include killed recombinantly modified microorganisms (whole cell recombinant bacterin vaccine), the latter including recombinant DNA encoding at least one protective protein (e.g., an antigenic protein) which has been expressed by the microorganisms prior to killing thereof. The protective protein(s) are operable to prevent or reduce the severity of a disease of the subject. The vaccine preparations of the invention do not require separation of the protective protein(s) from the host recombinant microorganism(s), thereby materially decreasing the complexity and cost of the vaccine formulations. A preferred vaccine against kennel cough includes recombinantly modified microorganisms which express protective antigens containing pertactin and filamentous hemagglutinin protein products.

5 Claims, No Drawings

OTHER PUBLICATIONS

Poynten, et al.; Serological Diagnosis of Pertussis: Evaluation of IgA Against Whole Cell and Specific *Bordetella pertussis* Antigens as Markers of Recent Infection; *Epidemiol Infect*; Apr. 2002; 128(2):161-7; Abstract.

Greenberg, et al.; Interchangeability of 2 Diphtheria-Tetanus-Acellular Pertussis Vaccines in Infancy; *Pediatrics*; Apr. 2002; 109(4):666-72; Abstract.

Van Loo, et al.; Multilocus Sequence Typing of *Bordetella pertussis* Based on Surface Protein Genes; *J. Clin Microbiol.*; Jun. 2002; 40(6):1994-2001; Abstract.

Abarca, et al.; [Immunogenicity and Reactogenicity of a Reduced Antigen Content Diphtheria, Tetanus and Acellular Pertussis Vaccine dTpa in 10 to 11 Years Old Children and in Adults]; *Rev Med Chil.*; May 2002; 130(5):502-10; Abstract.

Hellwig, et al.; Crucial Role of Antibodies to Pertactin in *Bordetella pertussis* Immunity; *J Infect Dis.*; Sep. 2003; 18895):738-42; Abstract.

Gzyl, et al.; [In Process Citation]: *Przegl Epidemiol*; 2003; 57(1):181-92; Abstract.

Trollfors, et al.; Determination of Pertactin IgG Antibodies for the Diagnosis of Pertussis; *Clin Microbiol Infect*; Jul. 2003; 9(7):585-9; Abstract.

Kourova, et al.; Comparison of HTE *Bordetella pertussis* and *Bordetella parapertussis* Isolates Circulating in Saint Petersburg Between 1998 and 2000 with Russian Vaccine Strains; *J Clin Microbiol.*; Aug. 2003; 41(8):3706-11; Abstract.

Ausiello, et al,; T-Cell Immune Response Assessment as Complement to Serology and Intranasal Protection Assays in Determining the Protective Immunity Induced by Acellular Pertussin Vaccines in Mice; *Clin Diagn Lab Immunol*; Jul. 2003; 10(4):637-42; Abstract.

Botet, et al.; Immunity and Safety in Infants of a DTwPHib Full Liquid; *Acta Paediatr*: May 2003: 92(5):541-5; Abstract.

Chapman, et al; Reduced-Antigen Combined Diphtheria-Tetanus-Acellular Pertussis Vaccine (Boostrix)*Drugs*; 2003; 63(13):1407-13; Discussion: 1415-6; Abstract.

De Schutter, et al.;Molecular Typing of *Bordetella pertussis* Isolates recovered From Belgian Children and Their Household Members; *Clin Infect Dis*; Jun. 2003; 36(11):139-6; Abstract.

Van Der Wielen, et al.; Seroprevalence of *Bordetella pertussis* Antibodies in Flanders (Belgium); *Vaccine*; Jun. 2003; 21(19-20):2412-7; Abstract.

Capiau, et al.; Development and Clinical Testing of Multivalent Vaccines Based on a Diphtheria-Tetanus-Acellular Pertussis Vaccine: Difficulties Encountered and Lessions Learned; *Vaccine*; Jun. 2003; 21(19-20):2273-87; Abstract.

Belloni, et al.; Immunogenicity of a Three-Component Acellular Pertussis Vaccine Administered at Birth; *Pediatrics*; May 2003; 111(5Pt 1): 1042-5; Abstract.

He, et al.; *Bordeltella pertussis* Protein Pertactin Induces Type-Specific Antibodies: one Possible Explanation for the Emergence of Antigenic Variants?; *J Infect Dis*; Apr. 2003; 187(8);: 1200-5; Abstract.

Curran, et al.; DTPa-HBV-IPV/Hib Vaccine (Infanrix HEXA)*Drugs*; 63(7):673-82; Discussion 683-4; Abstract.

Poirier, et al.; Collaborative Study for the Establishment of a European Phamacopoeia Biological Reference Preparation for *Bordetella pertussis* Mouse Antiserum for Serological Potency Testing of Acellular Pertussis Vaccines; *Biologicals*; Mar. 2003; 31(1):25-38; Abstract.

Ray, et al.; A High-Molecular-Weight Outer Membrane Protein of Xanthomonas Oryzae PV. Oryzae Exhibits Similarity to Non-Fimbrial Adhesins of Animal Pathogenic Bacteria and is Required for Optimum Virulence; *Mol Microbiol.*; Nov. 2002; 46(3):637-47; Abstract.

Zaretzky, et al.; Mechanism of Association of Adenylate Cyclase Toxin with the Surface of *Bordetell pertussis*; a Role for Toxin-Filamentous Haemagglutinn Interaction; *Mol Microbiol.*; Sep. 2002; 45(6):1589-98; Abstract.

Lorenzo-Pajuelo, et al.; Cavitary Pneumonia in an Aids Patient Caused by an Unusual *Bordetella bronchiseptica* Variant Producing Reduced Amounts of Pertactin and Other Major Antigens; *J Clin Microbiol.*; Sep. 2002; 40(9):3146-54; Abstract.

Sisti, et al.; Iin Vitro and In Vivo Characterization of a *Bordetella bronchiseptica* Mutant Strain with a Deep Rough Lipopolysaccharide Structure; *Infect Immun*; Apr. 2002; 70(4):1791-8; Abstract.

Denoel, et al.; Effects of Adsorptionof Acellular Pertussis Antigens Onto Different Aluminium Salts on the Protective Activity in an Intransala Murine Model of *Bordetella pertussis* Infection; *Vaccine*; Jun. 2002; 20(19-20):2551-5; Abstract.

Sheu, et al.; Characteristics and Potency of an Acellular Pertussis Vaccine Composed of Pertussis Toxin, Filamentous Hemagglutinn, and Pertactin; *J Microbiol Immunol*; Dec. 2001; 34(4):243-51; Abstract.

* cited by examiner

SEQUENCE LISTING

```
<160> NUMBER OF SEQ ID NOS: 8

<210> SEQ ID NO 1
<211> LENGTH: 15
<212> TYPE: PRT
<213> ORGANISM: Bordetella pertussis

<400> SEQUENCE: 1

Arg Gly His Thr Leu Glu Ser Ala Glu Gly Arg Lys Ile Phe Gly
1               5                   10                  15


<210> SEQ ID NO 2
<211> LENGTH: 15
<212> TYPE: PRT
<213> ORGANISM: Bordetella pertussis

<400> SEQUENCE: 2

Arg Gly His Thr Leu Glu Ser Ala Glu Gly Arg Lys Ile Phe Gly
1               5                   10                  15


<210> SEQ ID NO 3
<211> LENGTH: 33
<212> TYPE: DNA
<213> ORGANISM: Bordetella bronchiseptica

<400> SEQUENCE: 3

cgcggatccc tcccatcatc aaggccggcg agc                                  33


<210> SEQ ID NO 4
<211> LENGTH: 31
<212> TYPE: DNA
<213> ORGANISM: Bordetella bronchiseptica

<400> SEQUENCE: 4

tgctctagac tttcggcgta ccagagcgtc c                                    31
```

-continued

<210> SEQ ID NO 5
<211> LENGTH: 132
<212> TYPE: PRT
<213> ORGANISM: Bordetella bronchiseptica
<220> FEATURE:
<221> NAME/KEY: misc_feature
<222> LOCATION: (126)..(126)
<223> OTHER INFORMATION: Xaa can be any naturally occurring amino acid

<400> SEQUENCE: 5

```
Val His Leu Gln Arg Ala Thr Ile Arg Arg Gly Asp Ala Pro Ala Gly
1               5                   10                  15

Gly Gly Val Pro Gly Gly Ala Val Pro Gly Gly Phe Gly Pro Gly Gly
            20                  25                  30

Phe Gly Pro Val Leu Asp Gly Trp Tyr Gly Val Asp Val Ser Gly Ser
        35                  40                  45

Ser Val Glu Leu Ala Gln Ser Ile Val Glu Ala Pro Glu Leu Gly Ala
    50                  55                  60

Ala Ile Arg Val Gly Arg Gly Ala Arg Val Thr Leu Ser Gly Gly Ser
65                  70                  75                  80

Leu Ser Ala Pro His Gly Asn Val Ile Glu Thr Gly Gly Ala Arg Arg
                85                  90                  95

Phe Ala Pro Gln Ala Ala Pro Leu Ser Ile Thr Leu Gln Ala Gly Ala
            100                 105                 110

His Ala Gln Gly Lys Ala Leu Leu Tyr Arg Val Leu Pro Xaa Pro Val
        115                 120                 125

Lys Leu Thr Leu
    130
```

<210> SEQ ID NO 6
<211> LENGTH: 128
<212> TYPE: PRT
<213> ORGANISM: Bordetella bronchiseptica

<400> SEQUENCE: 6

```
Val His Leu Gln Arg Ala Thr Ile Arg Arg Gly Asp Ala Pro Ala Gly
1               5                   10                  15

Gly Ala Val Pro Gly Gly Ala Val Pro Gly Gly Phe Gly Pro Leu Leu
            20                  25                  30

Asp Gly Trp Tyr Gly Val Asp Val Ser Asp Ser Thr Val Asp Leu Ala
        35                  40                  45

Gln Ser Ile Val Glu Ala Pro Gln Leu Gly Ala Ala Ile Arg Ala Gly
    50                  55                  60

Arg Gly Ala Arg Val Thr Val Ser Gly Gly Ser Leu Ser Ala Pro His
65                  70                  75                  80

Gly Asn Val Ile Glu Thr Gly Gly Gly Ala Arg Arg Phe Pro Pro Pro
                85                  90                  95

Ala Ser Pro Leu Ser Ile Thr Leu Arg Ala Gly Ala Arg Ala Gln Gly
            100                 105                 110

Arg Ala Leu Leu Tyr Arg Val Leu Pro Glu Pro Val Lys Leu Thr Leu
        115                 120                 125
```

<210> SEQ ID NO 7
<211> LENGTH: 128
<212> TYPE: PRT
<213> ORGANISM: Bordetella bronchiseptica

<400> SEQUENCE: 7

-continued

```
Val His Leu Gln Arg Ala Thr Ile Arg Arg Gly Asp Ala Pro Ala Gly
1               5                   10                  15

Gly Ala Val Pro Gly Gly Ala Val Pro Gly Gly Phe Gly Pro Leu Leu
            20                  25                  30

Asp Gly Trp Tyr Gly Val Asp Val Ser Asp Ser Thr Val Asp Leu Ala
        35                  40                  45

Gln Ser Ile Val Glu Ala Pro Gln Leu Gly Ala Ala Ile Arg Ala Gly
    50                  55                  60

Arg Gly Ala Arg Val Thr Val Ser Gly Gly Ser Leu Ser Ala Pro His
65                  70                  75                  80

Gly Asn Val Ile Glu Thr Gly Gly Gly Ala Arg Arg Phe Pro Pro Pro
                85                  90                  95

Ala Ser Pro Leu Ser Ile Thr Leu Arg Ala Gly Ala Arg Ala Gln Gly
            100                 105                 110

Arg Ala Leu Leu Tyr Arg Val Leu Pro Glu Pro Val Lys Leu Thr Leu
        115                 120                 125


<210> SEQ ID NO 8
<211> LENGTH: 138
<212> TYPE: PRT
<213> ORGANISM: Bordetella bronchiseptica

<400> SEQUENCE: 8

Val His Leu Gln Arg Ala Thr Ile Arg Arg Gly Asp Ala Pro Ala Gly
1               5                   10                  15

Gly Ala Val Pro Gly Gly Ala Val Pro Gly Gly Ala Val Pro Gly Gly
            20                  25                  30

Ala Val Pro Gly Gly Phe Gly Pro Leu Leu Asp Gly Trp Tyr Gly Val
        35                  40                  45

Asp Val Ser Asp Ser Thr Val Asp Leu Ala Gln Ser Ile Val Glu Ala
    50                  55                  60

Pro Gln Leu Gly Ala Ala Ile Arg Ala Gly Arg Gly Ala Arg Val Thr
65                  70                  75                  80

Val Ser Gly Gly Ser Leu Ser Ala Pro His Gly Asn Val Ile Glu Thr
                85                  90                  95

Gly Gly Gly Ala Arg Arg Phe Pro Pro Pro Ala Ser Pro Leu Ser Ile
            100                 105                 110

Thr Leu Gln Ala Gly Ala Arg Ala Gln Gly Arg Ala Leu Leu Tyr Arg
        115                 120                 125

Val Leu Pro Glu Pro Val Lys Leu Thr Leu
    130                 135
```

KENNEL COUGH VACCINE

SEQUENCE LISTING

A printed Sequence Listing accompanies this application, and has also been submitted with identical contents in the form of a computer-readable ASCII file on a CD-Rom, the content and teachings of which are incorporated herein by reference. Each compact disc submitted herewith contains a file entitled 34826S~1.txt, created on May 24, 2004 and having a size of 6 KB.

BACKGROUND OF THE INVENTION

1. Field of the Invention

The present invention is broadly concerned with novel, low cost vaccine preparations, methods of preparing such vaccines and uses thereof. More particularly, the invention is concerned with vaccines and methods wherein the vaccines comprise recombinantly modified and killed microorganisms including therein recombinant DNA encoding at least one protective protein (e.g., an antigenic protein) and which has been expressed by the microorganism prior to killing thereof. These killed recombinant microorganisms can be directly administered as effective vaccines without the necessity of separation of the expressed protective protein(s) from the microorganisms, which has heretofore been considered essential.

2. Description of the Prior Art

A vast array of vaccines have been developed in the past to provide varying degrees of immunity against diseases. Generally speaking, prior vaccines have been in the form of preparations of dead or attenuated pathogenic microorganisms or antigenic substances extracted from them. In the case of bacterial vaccines, it has been known to genetically engineer bacteria to enhance their value as vaccines. Recombinant DNA techniques can also be used to generate attenuated strains, by deletion of pathogenesis-causing genes, or by engineering the protective epitope from a pathogen into a safe bacterium. It is also common to produce antigens or other protective proteins using conventional recombinant DNA techniques, wherein a plasmid or other appropriate vector is inserted into a bacterial host (e.g., *E. coli*) which then expresses the desired protein. While such engineered proteins can be effective biopharmaceutical vaccines, it has heretofore been thought essential that the expressed proteins be fully separated from the host recombinant microorganism(s) as a part of vaccine production. However, it is sometimes difficult and time consuming to perform such protein separations, and this significantly increases vaccine costs.

*Bordetella bronchiseptica* is a respiratory tract pathogen of dogs, pigs, cats, laboratory animals and humans. *B. bronchiseptica* can cause canine respiratory disease in the absence of prior or concurrent viral respiratory tract infection. Clinically, dogs with bordetellosis ("kennel cough") exhibit a soft, dry to severe paroxysmal cough and can develop extensive histopathological lesions including edema of the bronchial and retropharyngeal lymph nodes, marked polymorphonuclear infiltration of the respiratory tract mucosa and epithelial necrosis. Canine bordetellosis is remarkably similar to *pertussis* (whooping cough) caused by *Bordetella pertussis* infection of humans in terms of clinical disease, pathology and epidemiology. See, Keil, *Canine Bordetellosis: Improving Vaccine Efficiency Using Genetic and Antigenic Characterization of Bordetella Bronchiseptica Isolates from Dogs* (1999).

Kennel cough affects dogs of all ages, has a worldwide distribution, and can have an incidence as high as 50-90% in facilities housing large numbers of dogs. Outbreaks of kennel cough in vaccinated racing greyhounds and other dogs indicate that the disease continues to be a significant problem and that better vaccines are needed. Indeed, outbreaks in well-vaccinated dogs at racing tracks and kennels result in significant economic losses to the greyhound racing industry and at the very least are a periodic nuisance to dog owners, kennel managers and track administrators.

Current vaccines to prevent kennel cough include low-virulent live strains, whole-cell bacterins and undefined antigenic extracts, which are administered by various routes including parenterally and intranasally. Concerns about the efficacy and safety of current kennel cough vaccines have spurred the development of multivalent, acellular vaccines to prevent the disease. However, present-day vaccines do not provide sufficient disease control.

Filamentous hemagglutinin (FHA) is a secreted (but membrane associated) protein conserved within the genus *Bordetella* (Leininger et al. *Inhibition of Bordetella pertussis Filamentous Hemagglutining-mediated Cell Adherence with Monoclonal Antibodies*. FEMS Microbiology Letters 1993; 106:31-8.). The structural gene for the FHA of *B. pertussis* (fhaB) has been cloned and sequenced (Relman et al., *Filamentous hemagglutinin of Bordetella pertussis: nucleotide sequence and crucial role in adherence*. Proc Natl Acad Sci USA April 1989; 86(8):2637-41). FHA is essential for bacterial adherence to eukaryotic cells (Relman et al., *Filamentous hemagglutinin of Bordetella pertussis: nucleotide sequence and crucial role in adherence*. Proc Natl Acad Sci USA April 1989; 86(8):2637-41). Additionally, the immunologic response against FHA is protective in animal models of infection with *B. pertussis* (Locht et al. *The Filamentous Hemagglutining, a Multifaceted Adhesin Produced by Virulent Bordetella*. Supplemental Molecular Microbiology 1993; 9:653-60.; Brennan M J, and Shahin S. Pertussis. *Antigens That Abrogate Bacterial Adherence and Elicit Immunity*. American Journal of Respiratory Critical Care Medicine 1996; 154:S145-S149.).

While the protective benefits of FHA have been recognized for some time, the immunodominant regions have only recently been identified. Using a panel of monoclonal antibodies, Leininger et al. found two immunodominant domains (type I domain located near the COOH-terminus, type II domain located near the $NH_2$-terminus) within the FHA protein (Leininger et al. *Immunodominant Domain Present on the Bordetella pertussis Vaccine Component Filamentous Hemagglutining*. Journal of Infectious Disease 1997; 175: 1423-31.). Pepscan analysis, using monoclonal antibodies that recognized the type I immunodominant domain, indicated that the epitope for these antibodies was within the amino acid sequence RGHTLESAEGRKIFG (SEQ ID No. 1). Finally, convalescent whooping cough serum, as well as post vaccination serum, contained antibodies that specifically recognize the type I region of FHA.

In order to further characterize the antigenic makeup of the FHA of *B. pertussis*, Wilson et al. characterized polyclonal anti-FHA reactive clones identified in a phage display library (Wilson et al. *Antigenic Analysis of Bordetella pertussis Filamentous Hemagglutining with Phage Display Libraries and Rabbit Anti-filamentous Hemagglutining Polyclonal Antibodies*. Infectious Immunology 1998; 66:4884-94.). They determined that the portion of FHA between residues 1929-2019 contained the most immunodominant linear epitope of FHA. They also concluded that because this region contains a factor X homologue (Sandros and Tuomanen. *Attachment*

*factors of Bordetella pertussis: mimicry of eukaryotic cell recognition molecules. Trends Microbiol*, August 1993; 1(5): 192-6.) and the type I domain peptide defined by Leininger et al. (RGHTLESAEGRKIFG) (SEQ ID No. 2) peptides derived from this region are strong candidates for future protection studies.

Pertactin is the other protein used by *B. bronchiseptica* to adhere to the respiratory tract. Pertactin gets its name from the fact that it is the only protein that is capable, by itself, of inducing protective immunity against disease. Variations in nucleotide sequence, predicted amino acid sequence, and size of the pertactin proteins expressed in canine *B. bronchiseptica* isolates have been identified and have been confirmed from researchers working with swine strains of *B. bronchiseptica* as well as with strains of *B. pertussis* isolated from whooping cough cases. It is clear that canine vaccine strains of *B. bronchiseptica* and field isolates from vaccinated dogs with kennel cough do not express the same types of pertactin protein.

SUMMARY OF THE INVENTION

The present invention provides relatively low cost yet effective vaccines for administration to living subjects (e.g., mammals and birds) which comprise a quantity of recombinantly modified and killed microorganisms including therein recombinant DNA encoding at least one protective protein which has been expressed by the microorganism prior to killing thereof. The protective protein(s) are operable to prevent or reduce the severity of a disease of the subject.

In one aspect, the invention is predicated upon the discovery that safe and effective vaccines can be produced by administration of such killed, recombinantly modified microorganisms without the need for costly separation of the proteins expressed by the microorganisms. It has heretofore been thought that administration of these whole microorganisms would elicit unwanted immune responses or toxic reactions in the subjects, i.e., *E. coli* and other gram-negative bacteria contain endotoxic cell membrane components and other toxic proteins which would deleteriously affect a living subject if administered.

Vectors and Host Cells

The vaccines of the invention are usually in the form of cellular microorganisms containing therein a recombinant vector. A vector is a replicon, such as a plasmid, phage, or cosmid, into which another DNA segment may be inserted so as to bring about the replication of the inserted segment. The vectors of the invention are expression vectors, i.e., a vector that includes one or more expression control sequences that controls and regulates the transcription and/or translation of another DNA sequence.

In the expression vectors of the invention, the nucleic acid is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, vacteriophage, vaculoviruses, tobacco mosaic virus, herpes viruses, cytomegalovirus, retroviruses, poxyviruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The invention also provides host cells containing vectors of the invention. The term "host cell" is intended to include prokaryotic and eukaryotic cells into which a recombinant expression vector can be introduced. Usually the host cells are themselves non-pathogenic, but this is not essential. As used herein, "transformed" and "transfected" encompass the introduction of a nucleic acid molecule (e.g., a vector) into a cell by one of a number of techniques. Although not limited to a particular technique, a number of these methods are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfection host cells are found in Sambrook et al., *Molecular Cloning: a Laboratory Manual* (2nd edition), Cole Spring Harbor Laboratory, NY (1989), and reagents for transformation and/or transfection are commercially available (e.g., Lipofectin (Invitrogen/Life Technologies); Fugene (Roche, Indianapolis, Ind.); and SuperFect (Qiagen, Valencia, Calif.)).

In particularly preferred forms, the microorganisms of the invention are selected from the group consisting of bacteria and yeast, with bacteria such as *E. coli* being commonly employed. The vector of choice is normally an appropriate plasmid which expresses a fusion protein containing an antigenic protein or fragment. Vaccines in accordance with the invention may be monovalent or polyvalent as required. The vaccines may be administered to a variety of living subjects, especially those selected from the group consisting of mammals and birds, for example humans, livestock and domestic pets.

In the case of the preferred kennel cough vaccines of the invention, the vaccines include microorganisms which have recombinant DNA therein encoding protective proteins selected from the group consisting of pertactin and filamentous hemagglutinin proteins, fragments of such proteins, and mixtures thereof. Especially preferred kennel cough vaccines include killed *E. coli* having expression vectors therein which encode for fusion proteins having protein fragments selected from the group consisting of SEQ IDS Nos. 5, 6, 7, 8 and 9, and mixtures thereof.

Complete Vaccines

The vaccines of the invention can also include various pharmaceutically acceptable carriers, excipients and/or adjuvants. For example, complete vaccines can include buffers, stabilizers (e.g., albumin), diluents, preservatives, and solubilizers, and also can be formulated to facilitate sustained release. Diluents can include water, saline, dextrose, ethanol, glycerol, and the like. Additives for isotonicity can include sodium chloride, dextrose, mannitol, sorbitol, and lactose. Compositions can be formulated for particular routes of administration, including, for example, oral, intranasal, intramuscular, intra-lymph node, intradermal, intraperitoneal, or subcutaneous administration, or for a combination of routes.

In some embodiments, the vaccines can include an adjuvant. Suitable adjuvants can be selected based, for example, on route of administration and number of planned administrations. Non-limiting examples of adjuvants include mineral oil adjuvants such as Freund's complete and incomplete adjuvant, and Montanide incomplete seppic adjuvant (ISA, available from Seppie, Inc., Paris, France); oil-in-water emulsion adjuvants such as the Ribi adjuvant system (RAS); TiterMax®, and syntax adjuvant formulation containing muramyl dipeptide; or aluminum salt adjuvants.

Administration of Vaccines

The vaccines of the invention can be administered orally, transdermally, intravenously, subcutaneously, intramuscularly, intraocularly, intraperitoneally, intrarectally, intravaginally, intranasally, intragastrically, intratracheally, intrapulmonarily, or any combination thereof. The most preferred administration route is subcutaneous, especially for the kennel cough vaccines.

Suitable doses of the vaccine elicit an immune response in the subject but do not cause the subject to develop severe clinical signs of the particular viral infection. The dose required to elicit an immune response depends on the route of administration, the nature of the composition, the subject's size, weight, surface area, age, and sex, other drugs being administered, and the judgment of the attending practitioner. Wide variations in the needed dose are to be expected in view of the variety of compositions that can be produced, the variety of subjects to which the composition can be administered, and the differing efficiencies of various routes of administration. For example, oral administration would be expected to require higher doses than administration by intravenous injection. Variations in these dose levels can be adjusted using standard empirical routines for optimization, as is well understood in the art. Encapsulation of the composition in a suitable delivery vehicle (e.g., polymeric microparticles or implantable devices) may increase the efficiency of delivery, particularly for oral delivery.

To determine if an immune response was induced in the subject, a biological sample from the subject can be examined to determine if it contains detectable amounts of antibodies having specific binding affinity for one or more antigens of the particular organism the subject was vaccinated against. The biological sample can be blood (e.g., serum), a mucosal sample (e.g., saliva or gastric and bronchoalveolar lavages), or meat juice or meat exudate (i.e., the liquid that escapes from extra- and intracellular spaces when muscle tissues are frozen and thawed). Methods for detecting antibodies, including IgG, IgM, and IgA, are known, and can include, for example, indirect fluorescent antibody tests, serum virus neutralization tests, gel immunodiffusion tests, complement fixation tests, enzyme-linked immunosorbent assays (ELISA) or Western immunoblotting. In addition, in vivo skin tests can be performed on the subjects. Such assays test for antibodies specific for the organism of interest. If antibodies are detected the subject is considered to be seropositive.

Vaccinated subjects also can be tested for resistance to infection by the relevant organism. After immunization (as indicated above), the test subjects can be challenged with a single dose or various doses of the disease causing microorganism. The test subjects can be observed for pathologic symptoms familiar to those in the art, e.g., restlessness, dyspnea after exercise, neurological signs such as posterior weakness, paresis, ataxis, lameness, head pressing or hanging, aggressive behavior, morbidity, and/or mortality. Alternatively, they may be euthanized at various time points, and their tissues (e.g., lung, brain, spleen, kidney or intestine) may be assayed for relative levels of the virus using standard methods. The data obtained with the test subjects can be compared to those obtained with a control group of subjects. Increased resistance of the test subjects to infection relative to the control groups would indicate that the test vaccine is an effective vaccine. Thus, in some embodiments, a vaccinated subject is resistant to an infection upon challenge. That is, the subject does not develop severe clinical signs of the infection after being challenged with a virulent form of the disease causing microorganism. In other embodiments, a vaccinated subject exhibits an altered course of the infection. In still other embodiments, overall mortality from a particular microorganism in a group of subjects may be reduced.

DETAILED DESCRIPTION OF THE PREFERRED EMBODIMENTS

The following examples set forth preferred procedures for the development of recombinant microorganisms useful in the context of the invention, and in the production of specific vaccines against kennel cough. It is to be understood, however, that these examples are provided for illustrative purposes only, and nothing therein should be considered as a limitation upon the overall scope of the invention.

EXAMPLE I

Development of Pertactin Clone (PRN2)

Step 1—Growth of *Bordetella bronchiseptica* and Isolation of Genomic DNA

In this procedure, a known strain of *B. bronchiseptica* is struck for isolation on a room temperature Bordet-gengou plate, which was then incubated for 48 hr at 37° C. The plate was inspected at 24 and 48 hr to assure that growth is pure and colonies are isolated. *B. bronchiseptica* should form small, glossy, white, isolated colonies and appear mucoid where growth is dense. If growth was very heavy or the plate contaminated, the plate was restreaked for isolation from an area of least growth.

Pure, isolated colonies were observed, a single colony was inoculated into a 2 ml aliquot of 2 ml sterile nutrient broth in a 15 ml centrifuge tube. The tube was then capped tightly and vortexed. Next, the tube was incubated for 48 hr at 37° C., with shaking at 200 rpm. Thereupon, the culture was transferred to a 2 ml microcentrifuge tube. As a further assurance of purity, a loopful of the culture was separately streaked onto a BG plate and incubated for 24 hr The microcentrifuge tube was harvested by centrifugation at 13,000 rpm for 10 minutes. The supernatant was discarded, leaving an easily visible cell pellet.

One microliter (1 ml) of sterile purified water was added to the pellet and the tube was capped tightly and vortexed thoroughly to resuspend the pellet. The resulting suspension was then heated in a boiling water bath for 10 minutes. The heated product was then centrifuged at 13,000 rpm for 10 minutes and the supernatant was collected for use as template DNA in PCR.

Step 2—PCR of Pertactin Gene from Genomic DNA

This procedure involves amplification of the pertactin gene (PRN) from genomic DNA of *B. bronchiseptica* using the polymerase chain reaction (PCR). After analysis, the PCR product obtained is used for cloning.

The following cocktail was mixed in a microcentrifuge tube:

| | |
|---|---|
| 10× PCR buffer (without $MgCl_2$) | 25 μL |
| $MgCl_2$ (25 mM) | 5 μL |
| dNTPs (equal volume of all nucleotides) | 2 μL |
| Forward PCR primer (10 μM) | 6.25 μL |
| Reverse PCR primer (10 μM) | 6.25 μL |
| Taq DNA polymerase | 2.5 μL |
| Dimethyl sulfoxide (DMSO) | 25 μL |
| Water | 150 μL |

The forward primer had the sequence 5'-CGCGGATCCCTCCCATCATCAAGGCCGGCGAGC-3' (SEQ ID No. 3), whereas the reverse primer had the sequence 5'-TGCTCTAGACTTTCGGCGTACCAGAGCGTCC-3' (SEQ ID No. 4, and are based upon GenBank X54815 *B. bronchiseptica* sequence).

24 μL of the cocktail was aliquoted into each of 10 PCR tubes. 1.0 μL of water was added to the first tube, which served as a negative control. 1.0 μL of the genomic DNA from Step 1 was added to each of the remaining tubes. All tubes were then placed in a thermocycler. Amplification of PRN was carried out with the following thermocycler program: preheating at 95° C. for 3 minutes, followed by 30 amplification cycles of 20 seconds at 95° C., 30 seconds at 58° C. and 3 minutes at 72° C. The reaction was concluded with an extension cycle of 70° C. for 7 minutes.

Step 3—Analysis and Quantification of DNA by Agarose Gel Electrophoresis

In this protocol, the pertactin PCR product was analyzed using gel electrophoresis.

The casting gel was first prepared by pouring TBE into a large flask followed by addition of sufficient agarose needed to make a 1.2% gel (1.2 gm agarose per 100 mL of TBE). The suspension was then heated in a microwave oven until completely melted which generally involved microwaving the suspension for 20-30 seconds, followed by gentle swirling and further heating in 10-15 second bursts alternated with gentle swirling until the agarose melted. When the product was cool to the touch (approximately 55° C.) 2 μL Ethidium bromide stock solution was added followed by thorough swirling with the avoidance of bubble creation. Next, the mixture was slowly poured into a prepared casting stand, again without bubble creation. A comb was inserted into the agarose before it began to set, and the gel was allowed to solidify.

Following the instructions for the electrophoresis unit, the solidified gel was submerged in 1×TBE. Next a small aliquot (2-10 μL) of each sample, including markers, was prepared for electrophoresis by adding DNA loading dye in a ration of at least 1:6 dye to sample. The samples were then loaded into the wells, taking care not to overfill or allow bubble formation. This loading was done so as to ensure that the samples sank into the submerged wells. The unit was electrophoresed until the dye front moved two-thirds to three-fourths the length of the gel. Using a commercially available molecular weight marker (Lambda DNA digested with Eco RI and Hind III) the gel ran until the 1.904 Kb and 2.027 Kb bands separated. The gel was then gently separated from the casting tray and placed on a UV transilluminator and the size of the product was confirmed; at 1.7 Kb, (e.g. the pertactin PCR product was between the 1.904 Kb and 1.584 Kb marker bands.

Quantification of DNA was performed using a calibrated molecular weight marker in one of the agarose gel lanes. All-Purpose Hi-Lo DNA Marker was used. Conventional gel analysis software was employed to estimate the amount of DNA.

Step 4—Purification of PCR Products

In this step the PCR products were purified using a commercially available QIAquick Purification Kit.

First, the PCR products from Step 2 were pooled to obtain 100 μL of product. This was purified by following the kit manufacturer's instructions. In brief, PB buffer was added to the combined PCR product and the mixture was loaded into a QIAquick spin-column. This column was centrifuged with flow-through being discarded. The spin-column was washed with buffer PE and the PCR product was eluded with 50 μL purified water. A vacuum-equipped centrifuge was then used to dry the sample and the dried sample was resuspended in 10 μL purified water. As set forth above, the product was quantitated by electrophoresing.

Step 5—Quantification of DNA by UV Spectrophotometry

The spectrophotometer was warmed up following the manufacturer's directions, and the DNA was diluted in water to the volume required for the cuvettes being used. The spectrophotometer was zeroed using water as a no DNA reference control and absorbance of the samples were taken at 200 nm. The OD values were then converted to concentration of nucleic acid.

Step 6—Growth and Isolation of Plasmid DNA

Initially, a culture of *E. coli* containing expression vector plasmid pProEX Htb was prepared. A vial of the vector was thawed on ice, and the vector was streaked on room temperature LB agar supplemented with 50 μg/ml ampicillin. The streaked agar was incubated at 37° C. for 24 hr. The plate was then visually inspected to ensure that growth was pure and that colonies were isolated. The colonies were large (1-2 mm diameter), white, and smooth. If the growth were very dense, the plate was restreaked for isolation from an area of least growth. If the culture were deemed contaminated, it was discarded and the process begun again with frozen stock.

Next, 2 ml of the LB medium supplemented with 50 μg/ml ampicillin were aliquoted into a sterile, disposable, 15 ml tube. The tube was then inoculated with a single pProEX Htb colony, capped tightly and vortexed. The tube was then inoculated for 24 hr at 37° C. with shaking at 200 rpm. The 24 hr culture was then transferred to a 2 ml microcentrifuge tube. The culture was turbid, indicating a dense growth of bacteria. In order to confirm culture purity, a loopful of the culture was streaked onto a BG plate for isolation, followed by incubation at 37° C. for 24 hr. The microcentrifuge tube was centrifuged at 13,000 rpm for 10 minutes, in order to harvest cells. The supernatant was then discarded, leaving an easily visible pellet of 4-5 mm in diameter.

Plasmid DNA was isolated using a commercially available kit (QIAprep Miniprep by Qiagen) following the manufacturer's instructions. Briefly, the harvested cell pellet was treated with buffer P1, followed by buffer P2 and buffer N3. The resulting solution was passed through a spin-column and the column was washed with PE buffer. The plasmid DNA was then eluted in 50 μL purified water. A vacuum-equipped centrifuge was employed to dry the sample and the sample was then resuspended in 10 μL purified water. The 1 μL of resuspended plasmid DNA was quantified by electrophoresing as described above. Because plasmid DNA can be found in three states (linearized, circularized, or convoluted) the agarose gel may show up to three bands in the plasmid lane. Linearized plasmid runs slowest, so the band is at full length (ex. 4.2 kb). Circularized plasmid runs at about half-length (ex. 2.1 kb). Convoluted plasmid runs at about quarter-length (ex. 1 kb). A very good plasmid preparation with few broken, linearized plasmids, will not exhibit a full length band, and thus only half-length or half and quarter-length bands may appear.

If the concentration is greater than 100 ng/μL, the volume is adjusted with purified water so that the final concentration is 100 ng/μL. If the concentration is between 20 ng/μL and 100 ng/μL, the sample is discarded and the isolation sequence is repeated.

Step 7—Restriction Digestion of DNA

This procedure involves preparation of PCR product and vector for ligation using restriction enzyme digestion. The work is done on ice with water baths of 37° C. and 65° C. The restriction digestion of the PCR product was performed prior to ligation, and therefore the digestion of the PCR product and plasmid DNA were performed simultaneously. Two replicates of the plasmid DNA digestion were prepared, one to receive the PCR product insert and one for reference.

In the first step, 500 μL microcentrifuge tubes were labeled and chilled. The following was placed into each tube: 2 μL 10× Multicore buffer and sterile purified water. The tubes were mixed by tapping or using a pipette tip, and then returned to ice. Restriction enzymes (0.5 μL each BamHI and XbaI) were added to each tube, with mixing and an immediate return to ice. DNA samples were then added to the appropriate tubes, with mixing and immediate return to ice. The tubes were sealed with paraffin and placed in a floating tube rack, followed by incubation for three hours in the 37° C. water bath. The restriction enzymes were then inactivated by transferring the tubes to the 65° C. water bath for 10 minutes. A vacuum-equipped centrifuge was then employed to dry the samples. The dehydrated samples were then resuspended in 10 μL purified water. The samples were then quantified by electrophoresing 1 μL of the resuspended digested DNA as described above. If the concentration is greater than 10 ng/μL, the volume is adjusted with purified water to give a final concentration of 10 ng/μL. If the concentration is between 2 ng/μL and 10 ng/μL the sample may be used without further dilution. If the concentration is less than 2 ng/μL, it is discarded.

Step 8—Ligation of Restriction Digested DNA

This procedure describes the ligation of PCR product into a vector. The resultant recombinant DNA molecule is then introduced into *E. coli*. All work was done on ice, and the digested samples are the products from Step 7. The total volume of the ligation reaction mixture is 10 μL. In order to maximize the chances of success, ligations in several stoichiometric ratios of plasmid DNA to PCR product in the range of 1:2 top 1:10. First, microcentrifuge tubes were labeled and chilled. Using a DNA ligation kit the ligation was performed following manufacturer's instructions. This involved addition of 1 μL of 10× ligation buffer, 1 μL 10 mM rATP, purified water, digested PCR product (50 ng), digested plasmid DNA and 0.5 μL T4 DNA ligase (4 U/μL). In a no insert control, no PCR product was added. The tubes were incubated overnight at 4° C.

Step 9—Transformation of Recombinant DNA into *E. coli* Host

This procedure describes the cloning of recombinant DNA molecules into *E. coli*. Work was done on ice and competent cells were stored at −80° C. and protected from temperature fluctuation. Vials of cells were taken from the −80° C. freezer and placed on dry ice unless they were to be rapidly thawed for use as described below.

One 1.5 μL microcentrifuge tube was labeled and chilled for each ligation mixture from Step 8. A vial of competent cells (Maximum Efficiency *E. coli:* DH5αF'IQ) was removed from dry ice and thawed rapidly by rubbing between hands. 100 μL of cells were immediately dispensed into each chilled microcentrifuge tube. 5 μL of ligation mixture (from Step 8) were added to one tube, with mixing and immediately returned to ice. These steps were repeated with the ligation control mixture (self-ligation). The cell suspensions were maintained on ice for 10 minutes. The cells were then heat shocked by transferring the tubes to a 42° C. water bath for 2 minutes, whereupon the tubes were returned to ice. 1 mL LB broth (without ampicillin) was added to each tube, followed by incubation for 1 hr at 37° C., with shaking for each transformation reaction, an LB agar plate supplemented with 50 μg/mL ampicillin was labeled, and the plates were warmed to room temperature (if the agar surfaces were moist, they were placed in a hood with the lids opened for 5-10 minutes or until the agar surfaces appeared dry). After the 1 hr incubation 100 μL of each culture were transferred to the appropriate plate, using a sterile glass "L" or sterile disposable spreader to spread the cultures evenly over the agar surfaces. If the agar appeared wet, the lids were opened until the surfaces dried. The cultured plates were incubated for 12-16hr at 37° C.

Step 10—Screening of *E. coli* Colonies for Recombinant DNA

In this step the *E. coli* colonies are screened for the presence of recombinant DNA molecules.

The cultured plates from Step 9 were counted, and the number of colonies on each plate was recorded. More colonies were apparent on the PCR-plasmid plates than on self-ligation plates. Colonies were selected for screening, and for each such colony a 15 mL sterile, disposable centrifuge tube was prepared and labeled. 2 mL of LB broth supplemented with 50 μg/μL ampicillin was added to each tube, and each tube was inoculated with a single isolated colony. The tubes were then capped and vortexed, followed by incubation overnight at 37° C., with shaking at 200 rpm. Each culture sample was aseptically transferred to an appropriately labeled 2 mL microcentrifuge tube, which is capped and stored at 4° C. until completion of screening. The tubes were centrifuged at 13,000 rpm for 10 minutes to harvest the cells. Plasmid DNA is isolated from each sample using the QIAprep Miniprep Kit following the manufacturer's instructions, as indicated in Step 6. Next, the DNA was quantified as described in Step 3. The isolated DNA samples were digested with BamHI and XbaI following the procedure of Step 7. Agarose gels were prepared as described in Step 3. 5 μL of each digested sample was mixed with 5 μL DNA loading dye, and this mixture was loaded onto the gels as described in Step 3. Colonies that released 1.7 kb fragments upon BamHI-XbaI digestion were considered to be positive clones. The positive clones were retained whereas the remaining tubes were discarded. Samples of the positive clones were streaked onto LB agar plates supplemented with 50 mg/mL ampicillin, and the plates were incubated at 37° C. for 24 hr. The plates were checked for growth and stored at 4° C., until the clones were checked for protein expression.

The positive clones expressed a fusion protein containing a pertactin clone having a pertactin fragment partially characterized by SEQ ID No. 5, which is an immunoprotective region which corresponds with positions 281-408 of the GenBank sequence of *B. bronchiseptica* strain AY376325.

Buffers and Reagents

The following describe the preparation of various buffers and reagents used in the foregoing procedure:

Ampicillin Stock (50 mg/ml):

Dissolve 0.5 g of ampicillin powder (sodium salt) in 9 ml water.

Adjust the volume to 10 ml after the powder dissolves completely.

Filter sterilize.

Aliquot and store at −20° C.

DNA Loading Dye:

25 mg Bromophenol blue.

25 mg Xylene cyanol.

3 ml (v/v) Glycerol.

Adjust volume to 10 ml with purified water.

Mix thoroughly.

Aliquot and store at −20° C.

Ethidium Bromide:

Dissolve 1 g of Ethidium bromide in 10 ml purified water.

Stir for several hours to ensure dye is dissolved.

Aliquot.

Store in dark at room temperature.

Add 1 μl of to each 10 ml molten agarose.

Luria-Bertani (LB) Agar:

Dissolve 25 g of LB Broth powder in 950 ml purified H2O.

Add 25 g Bacto-Agar.

Mix thoroughly

Adjust volume to 1 l.

Aliquot into autoclavable containers.

Autoclave LB agar at 121° C., 15 psi for 30 minutes.

Pour plates immediately after agar has cooled to about 50° C. or store at room temperature in tightly closed bottles.

To melt agar that has solidified, microwave (alternate 15-30 sec microwave "bursts" with swirling until agar is melted). Cool the medium to 50° C. and immediately pour into Petri plates.

Luria-Bertani (LB) Agar Supplemented with Ampicillin:

Add ampicillin stock to 50° C. LB agar to a final concentration of 50 μg/ml.

Ampicillin stock=50 mg/ml, thus, 100 μL of stock is added to 100 ml of agar.

Alternatively, 25 μL of stock can be spread on the surface of an agar plate.

Luria-Bertani (LB) Broth:

Dissolve 25 g of LB Broth powder in 950 ml purified H2O.

Adjust volume to 1 l.

Autoclave LB Broth at 121° C., 15 psi for 30 minutes.

Store at room temperature in tightly closed bottles.

Luria-Bertani (LB) Broth Supplemented with Ampicillin:

To sterile LB Broth, add ampicillin stock as needed just before inoculation.

Nutrient Broth:

Dissolve 8 gm of Nutrient Broth powder in 1 l of purified water.

Mix well.

Aliquot into autoclavable bottles.

Autoclave at 121° C., 15 psi for 15 minutes.

Store at room temperature in tightly closed bottles.

10×TBE:

Pre-measured TBE salts are purchased from Amresco.

One package of 10×TBE salts is dissolved in 950 ml purified water.

Adjust volume to 1 l with purified water.

Mix well.

Aliquot into autoclavable bottles.

Autoclave at 121° C., 15 psi for 15 minutes.

Store at room temperature in tightly closed bottles.

1×TBE:

1×TBE can be obtained by diluting 10×TBE 1:10 with purified water (10 ml of 10×TBE plus 90 ml of purified water to make 100 ml of 1×TBE).

EXAMPLE II

Development of Pertactin Clones (PRN 1, 3 and 4)

In this example, three other pertactin clones were generated using three different *B. bronchiseptica* strains. The procedures of Example I were followed, including the use of the forward and reverse PCR primers (SEQ IDS Nos. 3 and 4).

The positive clones were found to express fusion proteins having pertactin fragments with the sequences of SEQ ID Nos. 6 (PRN 1), 7 (PRN 3) and 8 (PRN 4), which are respectively sequences of immunoprotective regions which corresponds with positions 281-408, 281-408 and 281-418, respectively, of the GenBank sequence of *B. bronchiseptica* strain AY376325.

EXAMPLE III

Development of Filamentous Hemagglutinin Truncated Protein (FHAt)

A truncated fusion protein (FHAt) was prepared which included a conserved domain homologous to the immunodominant region of FHA of *B. pertussis*. FHAt was shown to be safe and antigenic in rabbits and reduced the formation of antibodies that inhibited the hemagglutination associated with full length *B. pertussis* FHA. Briefly, polyclonal anti-*B. pertussis* FHA antiserum was used to identify an immunoreactive clone (pDK1) from the DNA library of a *B. bronchiseptica* field isolate. The insert of pDK1 was subcloned into a prokaryotic protein expression vector, to produce the FHAt fusion protein. The details of the procedure are set forth in the above-cited and incorporated by reference 1999 Keil thesis, Section V. This fusion protein had the sequence of SEQ ID No. 9, which is an immunoprotective region which corresponds with positions 1620-2070 of Genebank sequence M60351.

EXAMPLE IV

Vaccine Preparation

The positive *E. coli* clones produced pursuant to Examples I-III respectively bear plasmids which express protective *B. bronchiseptica* proteins, namely PRN2, PRN3 and FHAt.

Vaccine formulations were produced under standard commercial vaccine production conditions using the two pertactin clones (PRN2 and PRN3) and one filamentous hemagglutinin clone (FHAt). Briefly, the *E. coli* host cells bearing the PRN2, PRN3 and FHAt plasmids were grown in sterile culture media. Expression of the protective proteins was induced without extracellular secretion by the addition of IPTG. When the cultures reached log phase, growth was stopped by the addition of phenol to the media to kill the *E. coli*. After neutralization of the phenol, the cell suspensions were repeatedly washed with sterile saline, and the suspension(s)—either concentrated or diluted—to achieve a standard concentration. Three vaccine formulations were prepared, using equal volumes of the clones which were then combined with equal volumes of adjuvant (FHA) (proprietary light oil and water adjuvant).

The specific vaccine formulations were as follows:

Formulation 1=PRN2+FHAt

Formulation 2=PRN3+FHAt

Formulation 3=PRN2+PRN3+FHAt.

In order to assess the safety of the vaccines a 10× dose (10 ml) of Formulation 3 was injected into each of four dogs subcutaneously. Formulation 3 was used because it contained all of the components of the various formulations. The animals were observed for the onset of acute reactions every one to two hours over a period of four hours then with decreasing frequency. No systemic reactions occurred and all dogs remained normal in all regards. At 30 hr after injection, localized mild swelling was noted at the injection site of two animals. At one week, these two animals had developed sterile, localized, firm, non-painful swellings at the injection sites. These localized reactions were opened to allow for cleaning after which they healed rapidly.

In order to assess the immunogenicity of the vaccines, young Greyhounds were injected three times at approximately two week intervals with 1× doses (1 ml) of a formulation. Ten dogs received three doses of Formulation 1; nine received three doses of Formulation 2; and ten received three doses of Formulation 3. As with the previous experiment, all dogs that were vaccinated remained healthy and exhibited no systemic reactions to the vaccine formulations. In a few dogs, localized, firm, non-painful swellings developed at the injection site which resolved spontaneously without intervention. The reactions were characteristic of a type-III hypersensitivity reaction commonly associated with the use of some adjuvant in dogs.

Serum was collected from each dog prior to the first injection, at the time of each subsequent injection, and ten days after the final injection. Immune responses to the vaccines were assessed by purified protein ELISA.

In brief, ELISAs were performed as follows: PRN and FHA clones were grown and induced as described above. When the cultures reached log phase, the cells were harvested by centrifugation and lysed by ultrasonic exposure. PRN2, PRN3, and FHAt were separated from the cell lysates by nickel column chromatography. Wells of assay plates were coated with the purified proteins. Serum samples were diluted and applied in triplicate to the coated wells. Enzyme-linked secondary antibody was applied, followed by ABTS (colorimetric agent). Reactions as a measure of antibody concentration were evaluated by measuring the optical density of each well and averaging the triplicate wells.

The attached tables represent the results of the assays. The four serum samples from each Greyhound were tested against the antigens included in the vaccine the animal received. The results demonstrate that the animals' immune responses to the antigens increased after vaccination. Immune response to these antigens has been shown to be protective against *Bordetella bronchiseptica* infection.

All of the references noted herein are specifically incorporated by reference.

| | | PRN2 Day 1 | PRN2 Day 14 | PRN2 Day 30 | PRN2 Day 39 | | FHAt Day 1 | FHAt Day 14 | FHAt Day 30 | FHAt Day 39 |
|---|---|---|---|---|---|---|---|---|---|---|
| P2, P3, F | Dog 2 | 0.118 | 0.191 | 0.497 | 0.409 | Dog 2 | 0.500 | 0.537 | 1.567 | 1.546 |
| P2, P3, F | Dog 3 | 0.200 | 0.200 | 0.343 | 0.474 | Dog 3 | 0.740 | 0.957 | 1.237 | 1.756 |
| P2, P3, F | Dog 4 | 0.135 | 0.121 | 0.383 | 0.636 | Dog 4 | 0.671 | 0.912 | 1.688 | 1.740 |
| P2, P3, F | Dog 5 | 0.172 | 0.208 | 0.300 | 0.636 | Dog 5 | 0.600 | 0.685 | 1.187 | 1.522 |
| P2, P3, F | Dog 6 | 0.286 | 0.444 | 0.591 | 0.891 | Dog 6 | 0.316 | 0.785 | 1.562 | 1.783 |
| P2, P3, F | Dog 7 | 0.090 | 0.135 | 0.276 | 0.589 | Dog 7 | 0.316 | 0.785 | 1.562 | 1.783 |
| P2, P3, F | Dog 8 | 0.128 | 0.252 | 0.418 | 0.314 | Dog 8 | 0.594 | 1.477 | 1.912 | 1.649 |
| P2, P3, F | Dog 9 | 0.174 | 0.244 | 0.321 | 0.587 | Dog 9 | 0.939 | 1.466 | 1.599 | 1.831 |
| P2, P3, F | Dog 10 | 0.164 | 0.213 | 0.316 | 0.474 | Dog 10 | 0.772 | 1.071 | 1.595 | 1.693 |
| P2, P3, F | Dog 11 | 0.120 | 0.123 | 0.222 | 0.392 | Dog 11 | 0.203 | 1.053 | 1.452 | 1.598 |
| P2, F | Dog 12 | 0.104 | 0.159 | 0.220 | 0.715 | Dog 12 | 0.516 | 1.298 | 1.715 | 1.875 |
| P2, F | Dog 13 | 0.143 | 0.247 | 0.442 | 0.839 | Dog 13 | 0.896 | 1.346 | 1.764 | 1.883 |
| P2, F | Dog 14 | 0.124 | 0.188 | 0.205 | 0.484 | Dog 14 | 0.600 | 1.284 | 1.478 | 1.794 |
| P2, F | Dog 15 | 0.194 | 0.311 | 0.455 | 0.543 | Dog 15 | 0.907 | 1.766 | 1.780 | 1.883 |
| P2, F | Dog 16 | 0.227 | 0.270 | 0.314 | 0.557 | Dog 16 | 0.960 | 1.000 | 1.718 | 2.021 |
| P2, F | Dog 17 | 0.142 | 0.191 | 0.285 | 0.442 | Dog 17 | 0.889 | 1.499 | 1.659 | 1.951 |
| P2, F | Dog 18 | 0.099 | 0.211 | 0.598 | 1.099 | Dog 18 | 0.383 | 1.235 | 1.903 | 2.000 |
| P2, F | Dog 19 | 0.099 | 0.211 | 0.267 | 0.262 | Dog 19 | 0.411 | 0.800 | 1.318 | 1.545 |
| P2, F | Dog 20 | 0.092 | 0.092 | 0.143 | 0.419 | Dog 20 | 0.587 | 0.646 | 1.214 | 1.853 |
| P2, F | Dog 21 | 0.088 | 0.132 | 0.218 | 0.375 | Dog 21 | 0.371 | 0.621 | 1.430 | 1.865 |
| P3, F | Dog 23 | 0.071 | 0.096 | 0.100 | 0.246 | Dog 23 | 0.260 | 0.741 | 0.770 | 1.395 |
| P3, F | Dog 24 | 0.074 | 0.081 | 0.096 | 0.161 | Dog 24 | 0.252 | 0.558 | 0.580 | 1.108 |
| P3, F | Dog 25 | 0.076 | 0.114 | 0.209 | 0.226 | Dog 25 | 0.254 | 0.656 | 1.409 | 1.500 |
| P3, F | Dog 26 | 0.070 | 0.082 | 0.090 | 0.114 | Dog 26 | 0.148 | 0.276 | 0.276 | 0.758 |
| P3, F | Dog 27 | 0.090 | 0.132 | 0.300 | 0.466 | Dog 27 | 0.334 | 0.836 | 1.195 | 1.721 |
| P3, F | Dog 28 | 0.108 | 0.151 | 0.160 | 0.165 | Dog 28 | 0.428 | 0.766 | 2.033 | 2.100 |
| P3, F | Dog 29 | 0.067 | 0.105 | 0.208 | 0.499 | Dog 29 | 0.223 | 0.455 | 1.576 | 2.006 |
| P3, F | Dog 30 | 0.090 | 0.110 | 0.101 | 0.169 | Dog 30 | 0.318 | 0.460 | 0.658 | 0.876 |
| P3, F | Dog 31 | 0.179 | 0.180 | 0.190 | 0.200 | Dog 31 | 0.216 | 0.271 | 0.467 | 0.483 |
| | average all | 0.128 | 0.179 | 0.285 | 0.462 | average all | 0.504 | 0.905 | 1.390 | 1.639 |

| | | PRN3 Day 1 | PRN3 Day 14 | PRN3 Day 30 | PRN3 Day 39 |
|---|---|---|---|---|---|
| P2, P3, F | Dog 2 | 0.356 | 0.360 | 0.681 | 0.612 |
| P2, P3, F | Dog 3 | 0.474 | 0.651 | 0.750 | 1.079 |

-continued

| | | | | | |
|---|---|---|---|---|---|
| P2, P3, F | Dog 4 | 0.360 | 0.370 | 0.766 | 0.886 |
| P2, P3, F | Dog 5 | 0.451 | 0.460 | 0.527 | 0.623 |
| P2, P3, F | Dog 6 | 0.208 | 0.346 | 0.846 | 0.874 |
| P2, P3, F | Dog 7 | 0.208 | 0.346 | 0.548 | 0.874 |
| P2, P3, F | Dog 8 | 0.363 | 0.502 | 0.501 | 0.383 |
| P2, P3, F | Dog 9 | 0.799 | 0.800 | 0.853 | 1.083 |
| P2, P3, F | Dog 10 | 0.558 | 0.671 | 0.751 | 0.721 |
| P2, P3, F | Dog 11 | 0.184 | 0.342 | 0.496 | 1.071 |
| P3, F | Dog 23 | 0.159 | 0.334 | 0.360 | 0.346 |
| P3, F | Dog 24 | 0.201 | 0.234 | 0.243 | 0.314 |
| P3, F | Dog 25 | 0.241 | 0.328 | 0.326 | 0.274 |
| P3, F | Dog 26 | 0.149 | 0.241 | 0.260 | 0.280 |
| P3, F | Dog 27 | 0.232 | 0.413 | 0.474 | 0.584 |
| P3, F | Dog 28 | 0.278 | 0.280 | 0.367 | 0.380 |
| P3, F | Dog 29 | 0.154 | 0.165 | 0.270 | 0.414 |
| P3, F | Dog 30 | 0.250 | 0.263 | 0.302 | 0.293 |
| P3, F | Dog 31 | 0.167 | 0.435 | 0.526 | 0.550 |
| P2, F | Dog 12 | 0.431 | 0.786 | 0.800 | 0.939 |
| P2, F | Dog 13 | 0.399 | 0.810 | 1.137 | 1.342 |
| P2, F | Dog 14 | 0.831 | 1.221 | 1.321 | 1.360 |
| P2, F | Dog 15 | 0.802 | 0.982 | 1.006 | 1.200 |
| P2, F | Dog 16 | 0.570 | 0.590 | 0.902 | 0.990 |
| P2, F | Dog 17 | 0.611 | 0.824 | 0.816 | 0.742 |
| P2, F | Dog 18 | 0.187 | 0.242 | 0.250 | 0.260 |
| P2, F | Dog 19 | 0.344 | 0.520 | 0.560 | 0.580 |
| P2, F | Dog 20 | 0.555 | 0.391 | 0.375 | 0.492 |
| P2, F | Dog 21 | 0.223 | 0.211 | 0.278 | 0.407 |
| | average all | 0.371 | 0.487 | 0.596 | 0.688 |

I claim:

1. A kennel cough immunogenic composition for administration to dogs comprising an effective amount of a recombinantly modified and killed bacteria, said bacteria including therein transformed recombinant DNA expression vectors having DNA encoding protective proteins comprising the amino acid sequences set forth in SEQ ID Nos: 6, 7 and 9, said protective proteins having been independently expressed by the bacteria prior to killing thereof wherein said effective amount of said bacteria is capable of inducing an immune response in said dogs.

2. The immunogenic composition of claim 1, said bacteria being *E. coil.*

3. The immunogenic composition of claim 1, said expression vector being a plasmid vector within said bacteria.

4. The immunogenic composition of claim 1, including a pharmaceutically acceptable carrier.

5. The immunogenic composition of claim 1, including an adjuvant.

* * * * *